US009993658B2

(12) United States Patent
Browne et al.

(10) Patent No.: US 9,993,658 B2
(45) Date of Patent: Jun. 12, 2018

(54) LIGHT APPLICATORS, SYSTEMS AND METHODS

(71) Applicant: Yolo Medical Inc., Surrey (CA)

(72) Inventors: Gregory Vincent Browne, Victoria (CA); James Elliott Cameron, Victoria (CA); Trevor Pleydell-Bouverie Malcolm Moat, Victoria (CA); Christian Terry Proch McMechan, Victoria (CA)

(73) Assignee: YOLO Medical Inc., Surrey, CA (US)

( * ) Notice: Subject to any disclaimer, the term of this patent is extended or adjusted under 35 U.S.C. 154(b) by 537 days.

(21) Appl. No.: 13/968,124

(22) Filed: Aug. 15, 2013

(65) Prior Publication Data

US 2015/0051671 A1   Feb. 19, 2015

Related U.S. Application Data

(60) Provisional application No. 61/684,026, filed on Aug. 16, 2012.

(51) Int. Cl.
*A61N 5/06* (2006.01)
*A61N 5/00* (2006.01)

(52) U.S. Cl.
CPC ...... *A61N 5/0616* (2013.01); *A61N 2005/005* (2013.01); *A61N 2005/0643* (2013.01);
(Continued)

(58) Field of Classification Search
CPC ............... A61N 5/0625; A61N 5/0616; A61N 2005/005; A61N 2005/0643; A61N 2005/0659; A61N 2005/0662
(Continued)

(56) References Cited

U.S. PATENT DOCUMENTS 4,653,495 A   3/1987 Nanaumi
4,905,690 A   3/1990 Ohshiro
(Continued)

FOREIGN PATENT DOCUMENTS

KR   20-270882   4/2002
KR   20-274266   5/2002
(Continued)

OTHER PUBLICATIONS

Neira, R., et al., "Fat liquefication: effect of low level laser energy on adipose tissue", Plast Reconstr Surg, 2002, 110 (3):912-922.
(Continued)

*Primary Examiner* — Nathan J Jenness
*Assistant Examiner* — Boniface N Nganga
(74) *Attorney, Agent, or Firm* — Oyen Wiggs Green & Mutala LLP

(57) ABSTRACT

The present invention relates to light applicators, systems comprising light applicators, and methods for their use. One aspect of the invention provides a light applicator configured for contacting a portion of a subject's body surface and controllably applying light irradiation thereto. The light applicator comprises a housing, the housing comprising a treatment plate for contacting the portion of the subject's body surface and having one or more windows. One or more light emitters are disposed inside the light applicator and projecting toward the corresponding one or more windows of the treatment plate. A heat spreader plate is disposed inside the light applicator. One or more heat conducting members thermally connect the treatment plate to the heat spreader plate. The heat spreader plate is in physical contact with the one or more light emitters, thereby creating a heat conduction path from the one or more light emitters to the heat spreader plate, and to the treatment plate via the one or more heat conducting members.

24 Claims, 12 Drawing Sheets

(52) U.S. Cl.
CPC ............... *A61N 2005/0659* (2013.01); *A61N 2005/0662* (2013.01)

(58) Field of Classification Search
USPC .......................................................... 607/90
See application file for complete search history.

(56) References Cited

U.S. PATENT DOCUMENTS

| | | | |
|---|---|---|---|
| 4,930,504 A | 6/1990 | Diamantopoulos | |
| 5,150,704 A | 9/1992 | Tatebayashi | |
| 5,409,482 A | 4/1995 | Diamantopoulos | |
| 5,474,528 A | 12/1995 | Meserol | |
| 5,507,790 A | 4/1996 | Weiss | |
| 5,625,616 A * | 4/1997 | Koike | G11B 7/126 369/116 |
| 5,755,752 A | 5/1998 | Segal | |
| 5,879,376 A | 3/1999 | Miller | |
| 6,024,760 A | 2/2000 | Marchest | |
| 6,063,108 A | 5/2000 | Salansky | |
| 6,074,411 A | 6/2000 | Lai | |
| 6,106,516 A | 8/2000 | Massengill | |
| 6,273,884 B1 | 8/2001 | Altshuler | |
| 6,273,885 B1 | 8/2001 | Koop | |
| 6,306,130 B1 | 10/2001 | Anderson | |
| 6,322,584 B2 | 11/2001 | Ingle | |
| 6,413,267 B1 | 7/2002 | Dumoulin-White | |
| 6,461,866 B1 | 10/2002 | Whitehurst | |
| 6,517,532 B1 | 2/2003 | Altshuler | |
| 6,530,920 B1 | 3/2003 | Whitcroft | |
| 6,582,454 B2 | 6/2003 | Yayama | |
| 6,605,079 B2 | 8/2003 | Shanks | |
| 6,645,230 B2 | 11/2003 | Whitehurst | |
| 6,673,096 B2 | 1/2004 | Lach | |
| 6,676,655 B2 | 1/2004 | McDaniel | |
| 6,746,473 B2 | 6/2004 | Shanks | |
| 6,887,260 B1 | 5/2005 | McDaniel | |
| 7,033,381 B1 | 4/2006 | Larsen | |
| 7,060,061 B2 | 6/2006 | Altshuler | |
| 7,431,719 B2 | 10/2008 | Altshuler | |
| 7,959,656 B2 | 6/2011 | Myeong | |
| 2001/0011585 A1 | 8/2001 | Cassidy | |
| 2004/0006378 A1 | 1/2004 | Shanks | |
| 2004/0093042 A1 | 5/2004 | Altshuler | |
| 2004/0093047 A1 | 5/2004 | Lach | |
| 2004/0116984 A1 | 6/2004 | Spooner | |
| 2004/0133251 A1 * | 7/2004 | Altshuler | A61B 18/203 607/88 |
| 2004/0181210 A1 | 9/2004 | Shellman | |
| 2004/0236252 A1 | 11/2004 | Muzzi | |
| 2005/0203594 A1 | 9/2005 | Lim | |
| 2006/0095099 A1 | 5/2006 | Shanks | |
| 2006/0206176 A1 | 9/2006 | Shanks | |
| 2006/0224148 A1 | 10/2006 | Cho | |
| 2007/0073367 A1 | 3/2007 | Jones | |
| 2008/0108982 A1 | 5/2008 | Barolet | |
| 2008/0119831 A1 * | 5/2008 | Myeong | A61N 5/0613 606/13 |
| 2009/0287195 A1 * | 11/2009 | Altshuler | A61H 99/00 606/9 |
| 2010/0210993 A1 * | 8/2010 | Flyash | A61B 18/203 604/20 |
| 2012/0201007 A1 * | 8/2012 | Yeh | H05K 1/0203 361/719 |

FOREIGN PATENT DOCUMENTS

| | | |
|---|---|---|
| KR | 20-302173 | 1/2003 |
| KR | 20030000151 B1 | 1/2003 |

OTHER PUBLICATIONS

Neira, R., et al., "Fat liquefication: effect of low level laser energy on adipose tissue", Plast Reconstr Surg, 2002, 110 (3):923-925.

* cited by examiner

LIGHT APPLICATORS, SYSTEMS AND METHODS

TECHNICAL FIELD

The present invention relates to light irradiation of skin surfaces. More particularly, the invention relates to light applicators, systems comprising light applicators, and methods for their use.

BACKGROUND

Various devices, systems and methods are known for providing relaxation and/or therapeutic effects by irradiating a patient's body surface with light. Some example devices, systems and methods are described and illustrated in the commonly-assigned U.S. Pat. No. 7,959,656 and U.S. patent application Ser. No. 11/860,457, which are hereby incorporated by reference herein in their entirety.

SUMMARY OF THE INVENTION

Embodiments of the present invention are directed to light applicators, systems comprising light applicators, and methods for their use.

According to one aspect of the invention, there is provided a light applicator. The light applicator may comprise one or more solid-state light emitters for generating light to irradiate a subject's body surface. The solid-state light emitters may be laser diodes, LEDs (light emitting diodes), or some other solid-state light sources. In some embodiments, the light applicator may be a laser applicator having one or more light-emitting laser diodes. In some embodiments, the one or more solid-state light emitters may comprise one or more low-power light emitters. The term "low-power" herein means having a power output in the range of about 10 mW to about 100 mW. In some embodiments, the one or more solid-state light emitters may comprise one or more low-power light emitters having a power output in the range of about 30 mW to about 40 mW. In some embodiments, the one or more solid-state light emitters may comprise one or more medium-power light emitters. The term "medium-power" herein means having a power output in the range of about 80 mW to about 160 mW. When powered by suitable electric power, the one or more solid-state light emitters may emit light in the visible and/or infrared spectrum. For example, the light emitters may emit light in the range of 390 nm to 999 nm (for example, in the range of 635 nm to 680 nm, or in the range of 780 nm to 980 nm, or in some other range).

The light applicator is configured for contacting and irradiating a subject's body surface. The light applicator may comprise one or more electronic components (e.g., a control unit, a memory, one or more sensors, and circuitry) for at least one of generating, transmitting, recording, processing, storing and reporting electronic signals and/or other information useful for modulation of the light emitters.

In some embodiments, the light applicator is used independently. The light applicator may comprise an internal power supply (e.g., a battery).

In some embodiments, the light applicator is configured to communicate and cooperate with an external light control device. The light control device may comprise a power supply, a processor, a memory, circuitry, one or more input units (e.g., buttons, dials, keypad, keyboard, or touchscreen, etc.), one or more output units (e.g., a display screen). The light control device provides power for driving the light emitters. The light control device is also configured for at least one of generating, transmitting, recording, processing, storing and reporting electronic signals and/or other information useful for modulation of the light emitters.

According to one aspect of the invention, the light applicator comprises a housing which defines an internal compartment. The housing comprises a treatment plate for contacting a subject's body surface. The treatment plate has an outer side and the inner side. The outer side is the side for contacting a subject's body surface. The treatment plate comprises one or more windows. Windows could be openings (e.g., cutouts in the treatment plate) or could be covered or filled with a material substantially transparent to the light emitted by the light emitters. The light applicator also comprises one or more light emitters inside the housing, the one or more light emitters being configured to emit light toward the one or more windows of the treatment plate. The light applicator also comprises a heat spreader plate inside the housing. The heat spreader plate is in physical contact with one or more of the light emitters. In some embodiments, the treatment plate comprises one or more heat conducting members (e.g., bosses) extending on the inner side of the treatment plate, and the heat spreader plate is in physical contact with the one or more of the heat conducting members extending from the treatment plate. In some embodiments, the one or more heat conducting members (e.g., bosses) are part of the heat spreader plate and extend from the heat spreader plate to be in physical contact with the treatment plate. In some embodiments, both the heat spreader plate and the treatment plate comprise one or more heat conducting member (e.g., bosses), wherein the one or more heat conducting members of the heat spreader plate extend to contact the treatment plate and the one or more heat conducting members of the treatment plate extend to contact the heat spreader plate. In some particular embodiments, the one or more heat conducting members of the heat spreader plate extend to contact the corresponding one or more heat conducting members of the treatment plate. In some embodiments, the one or more heat conducting members are independent structures separate from the heat spreader plate and the treatment plate, but are in physical contact with both the heat spreader plate and the treatment plate. The contacts between the heat spreader plate and the light emitters and between the heat spreader plate and the treatment plate via the heat conducting members thereby create a heat conduction path from the one or more of the light emitters to the treatment plate via the heat spreader plate. The heat spreader plate and the treatment plate and the heat conducting members are made of a thermally conductive material, e.g., aluminum.

The heat spreader plate may be maintained in physical contact with the one or more of the light emitters and the one or more heat conducting members due to the physical dimensions of these parts and the constraints imposed by their arrangement and the dimensions of the internal compartment defined by the housing. Additionally or alternatively, the heat spreader plate may be maintained in physical contact with the one or more of the light emitters and the one or more heat conducting members by fastening means.

In some embodiments, the heat spreader plate comprises one or more openings therein corresponding to the one or more light emitters. Each one of the one or more light emitters is at least partially located in a corresponding one of the one or more openings in the heat spreader plate. Each one of the one or more light emitters has at least a portion that is in physical contact with a wall of the corresponding one of the one or more openings in the heat spreader plate.

In some embodiments, each light emitter has a head portion and a bezel portion. The bezel portion of each one of the light emitters is located in a corresponding one of the openings and is held in physical contact with the wall of the opening. The wall of the opening may have a shape that conforms to the shape of the light emitter or the bezel portion thereof to achieve good thermal contact.

In some embodiments, it is not required to have the heat spreader component as an intermediate medium. The heat conducting members (e.g., bosses) could interface directly with the individual light emitters. In some embodiments, it is also possible to have the light emitters arranged in such a manner that the light emitters contact directly with the treatment plate or some other part of the housing of the light applicator, without having heat conducting members (e.g., bosses) or the heat spreader plate.

Although some embodiments of the present invention utilizes the patient as a heat sink, it is not mandatory that the outer case of the light applicator that is not directly apposed on the patient be either rigid or thermally conductive. For example, the outer case of the light applicator may be made of a flexible or elastomeric material into which a thermally conductive treatment surface (or treatment surfaces) could be located. For example, a light applicator according to some embodiment may be designed like a "belt" wherein there are multiple "treatment faces" located in a longer "belt" form.

In some embodiments, the light applicator comprises a printed circuit board inside the housing. The one or more light emitters may be mounted on the printed circuit board. The one or more electronic components (e.g., a control unit, a memory, one or more sensors, and circuitry) may also be mounted on the board. The one or more electronic components may function to communicate with the external light control device and/or sense or modulate one or more parameters of the light emitters and/or process and store information. The printed circuit board may comprise a connector which connects the light applicator to the external light control device. In some embodiments, the connector may be a wireless connector which enables the light applicator to communicate with the light control device wirelessly.

In some embodiments, the light applicator comprises at least two printed circuit boards inside the housing: a first printed circuit board and a second printed circuit board. Either the first printed circuit board or the second printed circuit board or both may comprise the electronic components for communicating with the external light control device and/or sensing or modulating one or more parameters of the light emitters and/or processing and storing information. In some particular embodiments, the one or more light emitters are mounted on the first printed circuit board, and the electronic components for communicating with the external light control device and/or sensing or modulating one or more parameters of the light emitters and/or processing and storing information are mounted on the second printed circuit board.

In some embodiments, the first printed circuit board and the second printed circuit boards are spaced apart from each other inside the housing, and the heat spreader plate is disposed between the first printed circuit board and the second printed circuit board. For example, the second printed circuit board may be disposed in a space between the treatment plate and the heat spreader plate.

In some embodiments, the light applicator may comprise one or more printed circuit boards, and one of the one or more printed circuit boards may be disposed between the treatment plate and the heat spreader plate. The printed circuit board between the treatment plate and the heat spreader plate may comprise one or more openings which allow the one or more corresponding heat conducting member (of the treatment plate and/or the heat spreader plate) to extend through the one or more openings such that the heat spreader plate and the treatment plate are thermally connected via the one or more heat conducting members. With this configuration, a heat conducting path from the heat spreader plate to the treatment plate via the heat conducting members is maintained despite the presence of the second printed circuit board between the heat spreader plate and the treatment plate.

In some embodiments, the heat spreader plate comprises one or more openings corresponding to the one or more light emitters of the light applicator. The heat spreader plate is disposed between the first printed circuit board and the second printed circuit board. The one or more light emitters are mounted on the first printed circuit board. The one or more light emitters may extend from the first printed circuit board through the one or more corresponding openings in the heat spreader plate and toward the second printed circuit board and the treatment plate. In some embodiments, each light emitter has a head portion and a bezel portion. The bezel portion of each one of the light emitters is located in one of the corresponding openings and is held in physical contact with the wall of the opening. The wall of the opening may have a shape that conforms to the shape of the light emitter or the bezel portion thereof to achieve good thermal contact.

According to one aspect of the invention, there is provided a lipolysis system comprising at least one light applicator as described herein, and a light control device which comprises hardware, circuitry and software configured for at least one of generating, transmitting, recording, processing, storing and reporting electronic signals and/or other information for controlling operation of the light emitters of the at least one light applicator. In some embodiments, the system comprises a plurality of light applicators, each one of the light applicators in communication with the light control device. The light control device may comprise a power supply, a processor, a memory, circuitry, one or more input units (e.g., buttons, dials, keypad, keyboard, or touchscreen, etc.), and one or more output units (e.g., a display screen). The power supply of the light control device provides power to the light emitters of the light applicators.

According to one aspect of the invention, there are provided methods for the use of the lipolysis systems and/or the light applicator of the present invention. In some embodiments, the method comprises contacting the treatment plate of the light applicator with a target portion of a subject's body surface, turning on the light emitters of the light applicator, and providing light irradiation of the target portion of the subject's body portion for a selected period of time. The method may comprise conducting heat generated from the light emitters to the treatment plate and further to the subject's body surface. The method may also comprise manipulating an external light control device to communicate with the light applicator to regulate the light emitters of the light applicator. The method may comprise manually or automatically modulating the light output by the light emitters of the light applicator. Modulating the light emitted by the light applicator may comprise modulating the current and/or voltage and/or some other parameter of the electric power supplied to the light emitters of the light applicator. The method may also comprise monitoring one or more parameters of the light emitters and modulating one or more parameters of the light emitters based on the information obtained from the monitoring. The method may comprise modulating one or more parameters of the light emitters to maintain the light emitters at a predetermined temperature or within a predetermined temperature range. In some embodiments, the method comprises contacting a plurality of light applicators with a plurality of target portions of a subject's body surface for application of light irradiation thereto.

Further aspects of the invention and features of various example embodiments of the invention are described below.

BRIEF DESCRIPTION OF DRAWINGS

In drawings which show non-limiting embodiments of the invention:

In FIG. 2, the treatment plate is shown on top.

In FIG. 3, the back plate is shown on top.

In FIG. 4, the treatment plate is shown on top.

In FIG. 5, the back plate is shown on top.

In FIG. 7, the treatment plate is shown on top.

In FIG. 8, the back plate is shown on top.

In FIG. 9, the treatment plate is shown on top.

In FIG. 10, the back plate is shown on top.

DETAILED DESCRIPTION

Figure 1:
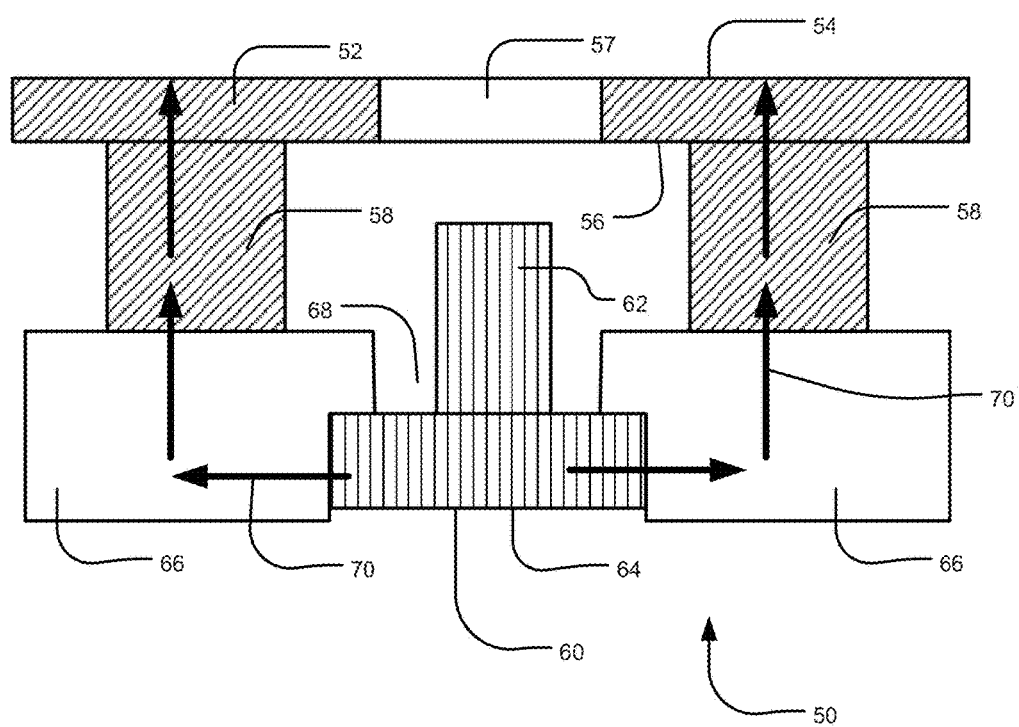
FIG. 1 is a cross-sectional view of a portion of an example light applicator according to an example embodiment of the present invention.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Aspects of the present invention provide a light applicator for contacting and controllably irradiating a portion of a subject's body surfaces with light in the visible and/or infrared spectrum, systems comprising one or more of the light applicators communicating with a light control device, and methods for the use of the applicators and/or the systems. The light applicator comprises one or more solid-state light emitters. In some embodiments, the light applicator is a laser applicator which comprises one or more light emitting laser diodes.

The inventors have determined that providing laser diodes or some other solid-state light emitters to irradiate a subject's body surface may lead to considerable amounts of heat being generated from the light emitters during prolonged application of light. In some instances, the light applicator may overheat, causing the light applicator to fail or malfunction. The inventors have determined that when the light emitters are overheated, the quality and/or quantity of light output become inconsistent thereby reducing treatment efficacy. Overheating of the light emitters may also reduce the lifetime of the light emitters. Also, light output varies with temperature so changes in temperature can result in variations in light output. For example, in a case where a light applicator is used to provide a series of treatments, the first treatment when light emitters are cool may provide increased light output while later treatments after the light emitters have heated up may provide reduced light output. This can be a significant problem. The inventors have determined that it is desirable to develop light applicators wherein the light emitters can be maintained at a relatively constant temperature so that the light outputs of the light emitters can be maintained at desired levels during prolonged application of light.

The inventors have determined that it is desirable to conduct the heat generated by the light emitters to an outer surface of the light applicator, and subsequently into the subject's body surface when the light applicator is in contact with the subject's body surface. In many cases the light emitters will generate enough heat that it is impractical to rely on air conduction from relatively small light applicators to maintain thermal equilibrium with the light emitters kept at suitable operating temperatures. A subject's body can serve as an effective heat sink for the amount of heat emitted by a typical light applicator. The heat may be effectively transferred to the subject's body by thermal conduction when the light applicator is in direct contact with the subject's skin.

FIG. 1 is a cross-sectional view of a portion of an example light applicator 50 according to one example embodiment of the invention. Light applicator 50 has a heat conducting path 70 from light emitter 60 to an outer surface of the light applicator which is configured to contact a subject's body surface. Light applicator 50 comprises a treatment plate 52. Treatment plate 52 has an outer side 54 and an inner side 56. Treatment plate 52 has a window 57. Outer side 54 of treatment plate 52 is for contacting a subject's body surface.

Treatment plate 52 comprises a heat conducting member 58 that extends from inner side 56 of treatment plate 52. Heat conducting member 58 may be in the shape of a hollow cylinder. Light applicator 50 comprises a light emitter 60. Light emitter 60 has a head portion 62 and a bezel portion 64. Bezel portion 64 is in thermal contact with active elements of light emitter 60 such that temperature of the active elements of light emitter 60 can be controlled by removing heat by way of bezel portion 64. Light applicator 50 comprises a heat spreader plate 66. Heat spreader plate 66 is in physical contact with heat conducting member 58. Heat spreader plate 66 is also in physical contact with bezel portion 64 of light emitter 60. In the illustrated embodiment, heat spreader plate 66 comprises an opening 68. Bezel portion 64 of laser diode 60 is located inside opening 68. Bezel portion 64 is in physical contact with a wall of opening 68. The wall of opening 68 may be shaped to conform to the shape of light emitter 60 or bezel portion 64 to achieve good thermal contact.

Light emitter 60 is located such that light rays or some of the light rays generated by light emitter 60 can pass through window 57 and transmit to the outside of light applicator 50. For example, a top portion of head portion 62 of light emitter 60 may extend out of opening 68 and into a space defined by heat conducting member 58 and in proximity of window 57. The contacts between heat spreader plate 66 and light emitter 60 and between heat spreader plate 66 and heat conducting member 58 of treatment plate 52 thereby create a heat conduction path 70 (indicated by arrows in FIG. 1) from light emitter 60 via heat spreader plate 66 and heat conducting member 58 to treatment plate 52.

Heat spreader plate 66 may be maintained in physical contact with light emitter 60 and heat conducting member 58 of treatment plate 52 due to the physical dimensions of these parts and the constraints imposed by their arrangement within light applicator 50. Additionally or alternatively, heat spreader plate 66 may be maintained in physical contact with light emitter 60 and heat conducting member 58 by fastening means (not shown in FIG. 1).

Figure 1A:
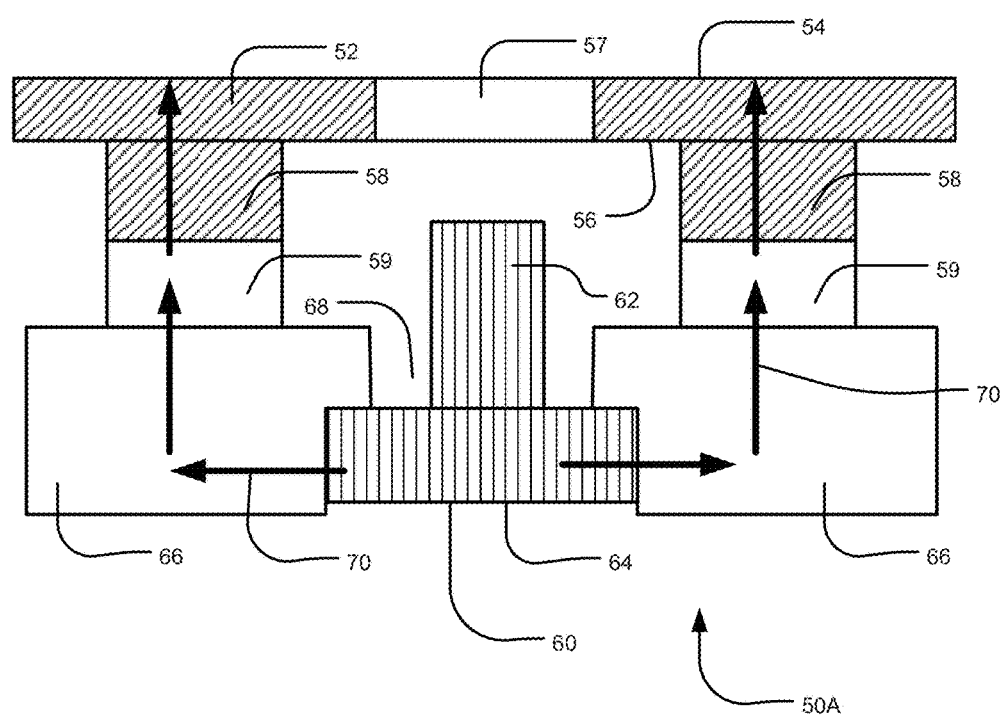
FIG. 1A is a cross-sectional view of a portion of an example light applicator according to another example embodiment of the present invention.

FIG. 1A is a cross-sectional view of a portion of another example light applicator 50A. Light applicator 50A is similar to light applicator 50. However, in light applicator 50A, heat conducting member 58 extend from treatment plate 52, heat conducting member 59 extend from heat spreader plate 66, and heat conducting members 58, 59 extend toward one another and come into physical contact.

Figure 1B:
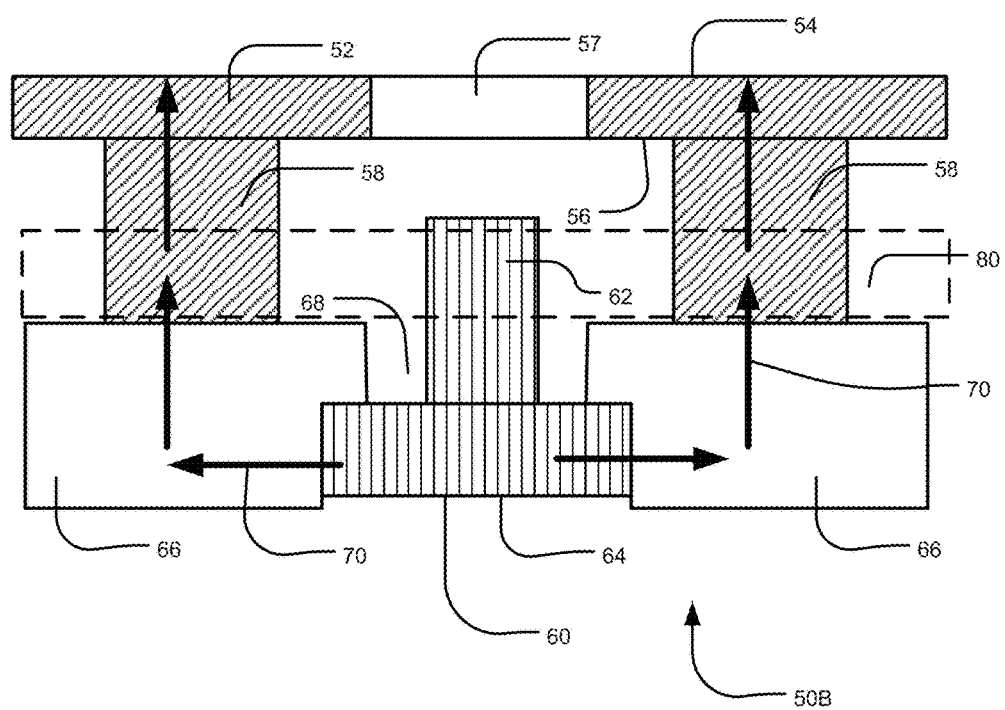
FIG. 1B is a cross-sectional view of a portion of an example light applicator according to another example embodiment of the present invention.
Figure 2:
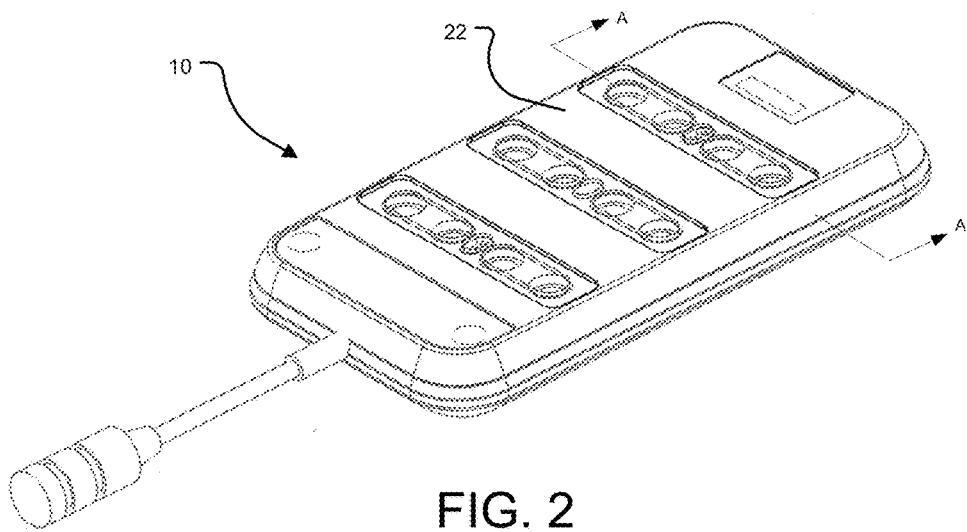
FIG. 2 is a perspective view of a light applicator according to another example embodiment of the present invention.
Figure 3:
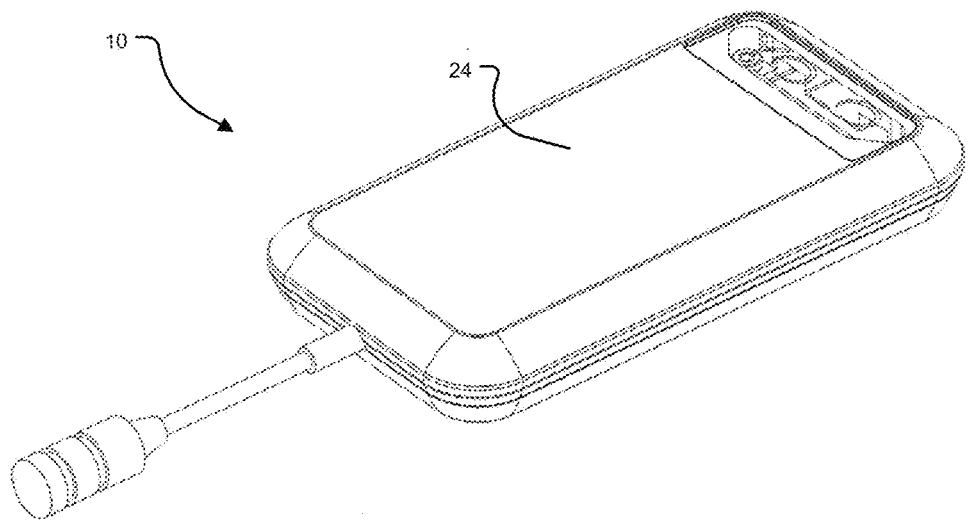
FIG. 3 is a perspective view of the FIG. 2 light applicator.
Figure 4:
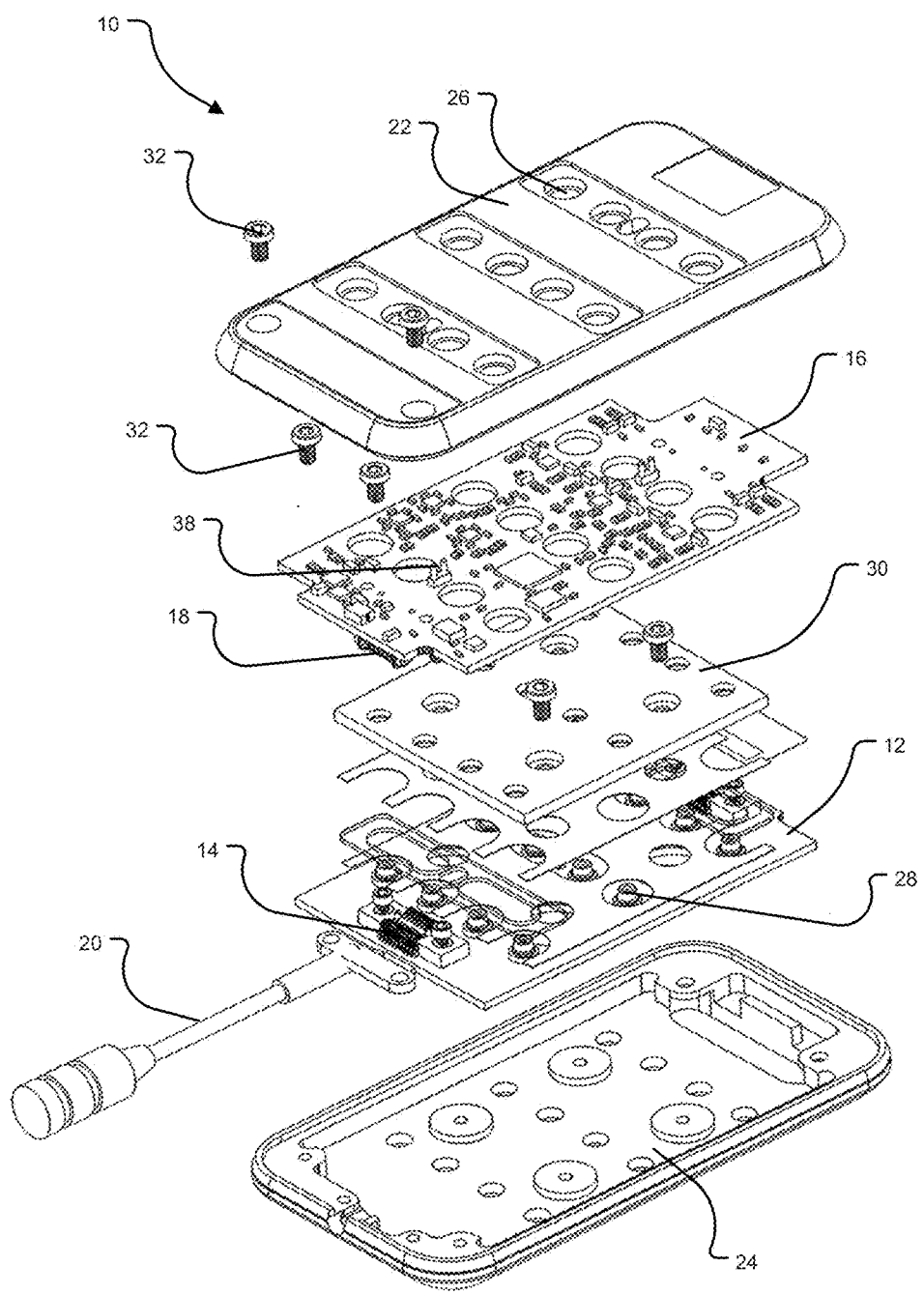
FIG. 4 is an exploded perspective view of the FIG. 2 light applicator.

FIG. 1B is a cross-sectional view of a portion of another example light applicator 50B. Light applicator 50B is similar to light applicator 50. In FIG. 1B, an example printed circuit board 80 is schematically shown. In FIG. 1B, printed circuit board 80 is disposed in a space between treatment plate 52 and heat spreader plate 66.

An example light applicator 10 according to one example embodiment of the invention is illustrated in FIGS. 2-6. One of the advantageous features of light applicator 10 is that it provides heat conducting paths which allow heat generated by light emitters (e.g., laser diodes 28) to be efficiently transferred to the subject's body surface and into the subject's body, thereby preventing overheating or temperature variation of the light emitters. The light applicator 10 comprises a diode printed circuit board (diode PCB) 12 which comprises a power connector 14 for receiving power from a power supply, and a control printed circuit board (control PCB) 16 which comprises a control connector 18. Power connector 14 and control connector 18 may be connected via a cable 20 with a light control device 230 (shown in FIG. 11). Laser diodes 28 are mounted on diode PCB 12. Control PCB 16 may comprise onboard electronic components for sensing one or more parameters of laser diodes 28 and/or switching on or off laser diodes 28 and/or processing and storing information as described in more detail below.

Light applicator 10 comprises a treatment plate 22 and a back plate 24. In an assembled state, treatment plate 22 and back plate 24 form a housing which houses diode PCB 12 and control PCB 16 and other components of light applicator 10 which are described further below.

Treatment plate 22 comprises one or more spaced-apart windows 26. Windows 26 could be openings or could be covered or filled with a material transparent to light from laser diodes 28. One or more laser diodes 28 are electrically connected to diode PCB 12. A heat spreader plate 30 is disposed between control PCB 16 and diode PCB 12. Control PCB 16, heat spreader plate 30, and diode PCB 12 all have one or more apertures which correspond to the positions of the one or more laser diodes 28. In an assembled state, laser diodes 28 extend from diode PCB 12, through the corresponding apertures of heat spreader plate 30 and control PCB 16 and toward windows 26 of treatment plate 22. The assembly of these parts of light applicator 10 may be enabled by fasteners, e.g., fasteners 32. Fasteners 32 also can clamp the various parts together to ensure good thermal contact and heat transfer.

Figure 5:
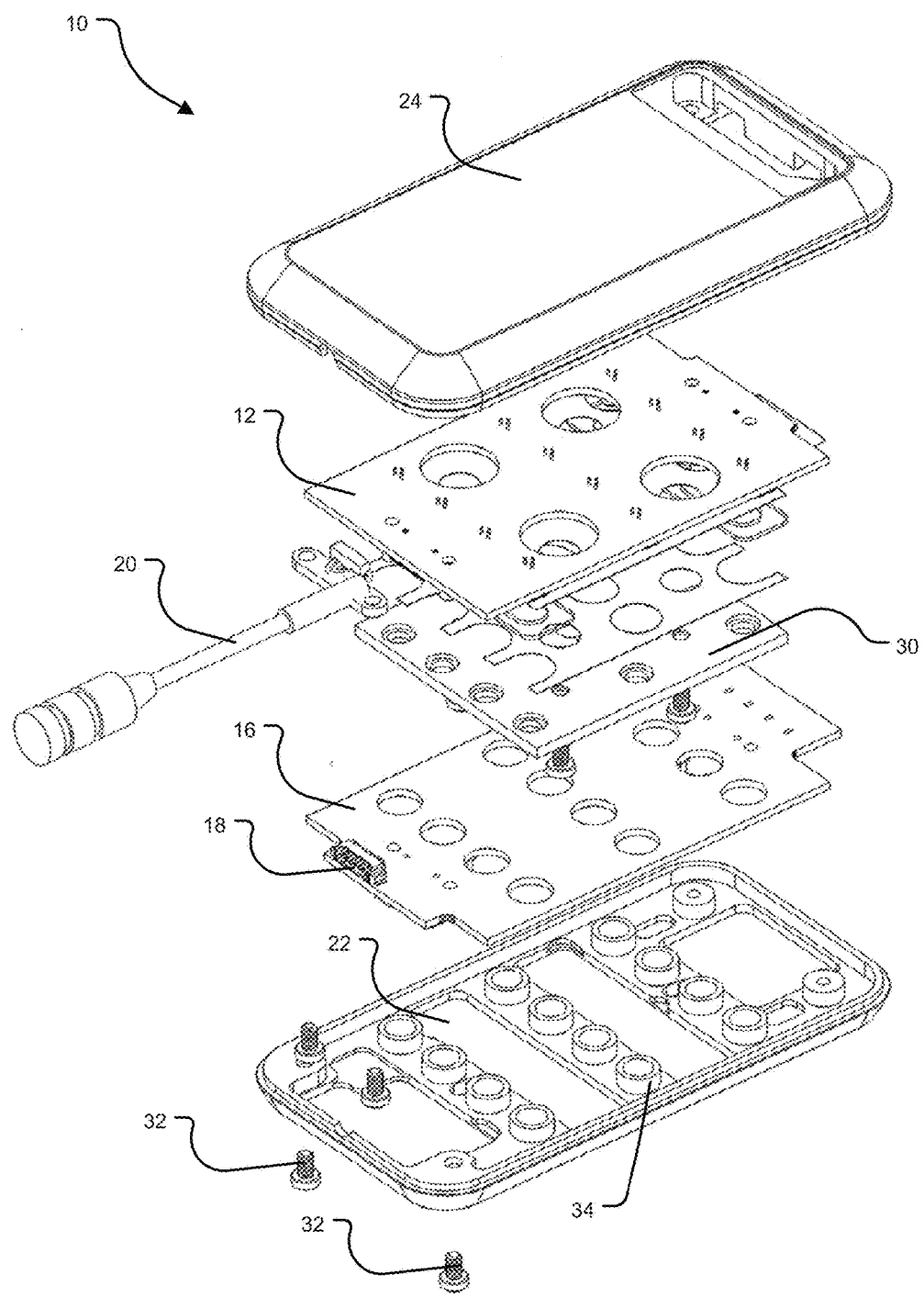
FIG. 5 is an exploded perspective view of the FIG. 2 light applicator.
Figure 6:
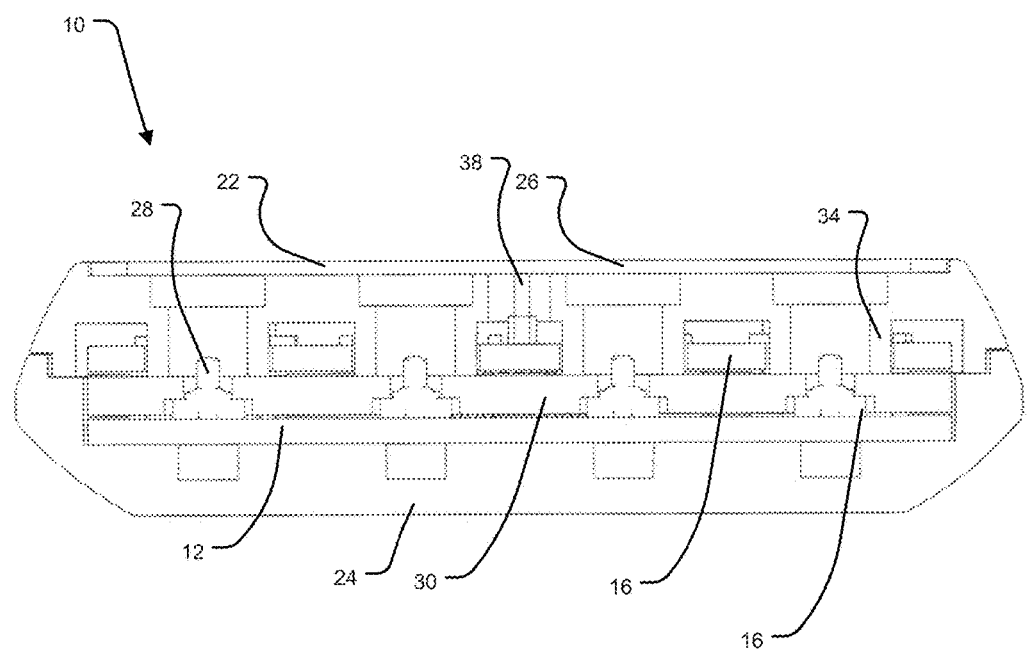
FIG. 6 is a cross-sectional view of the FIG. 2 light applicator, taken along lines A-A in FIG. 2.
Figure 7:
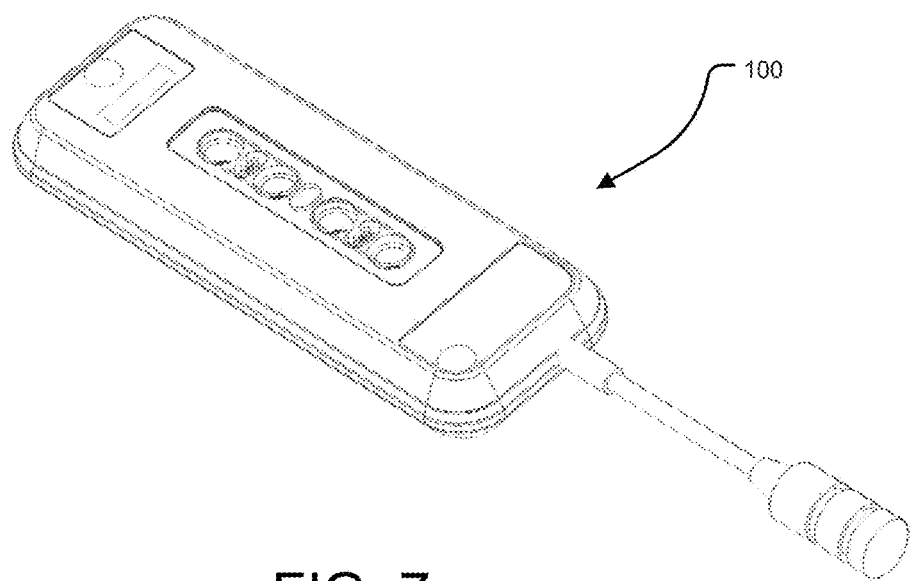
FIG. 7 is a perspective view of a light applicator according to another example embodiment of the present invention.
Figure 8:
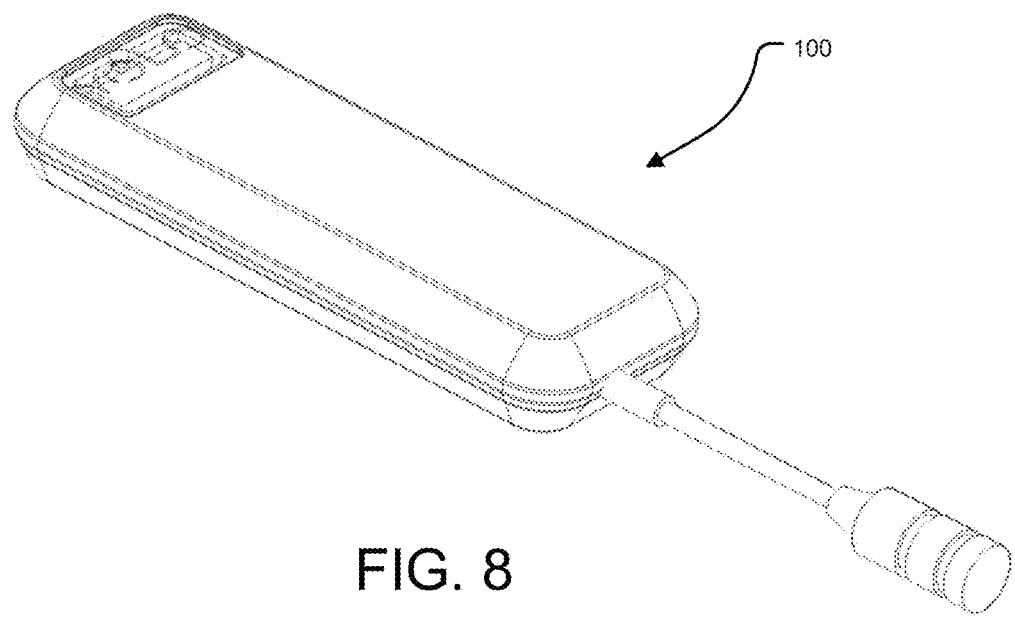
FIG. 8 is a perspective view of the FIG. 7 light applicator.
Figure 9:
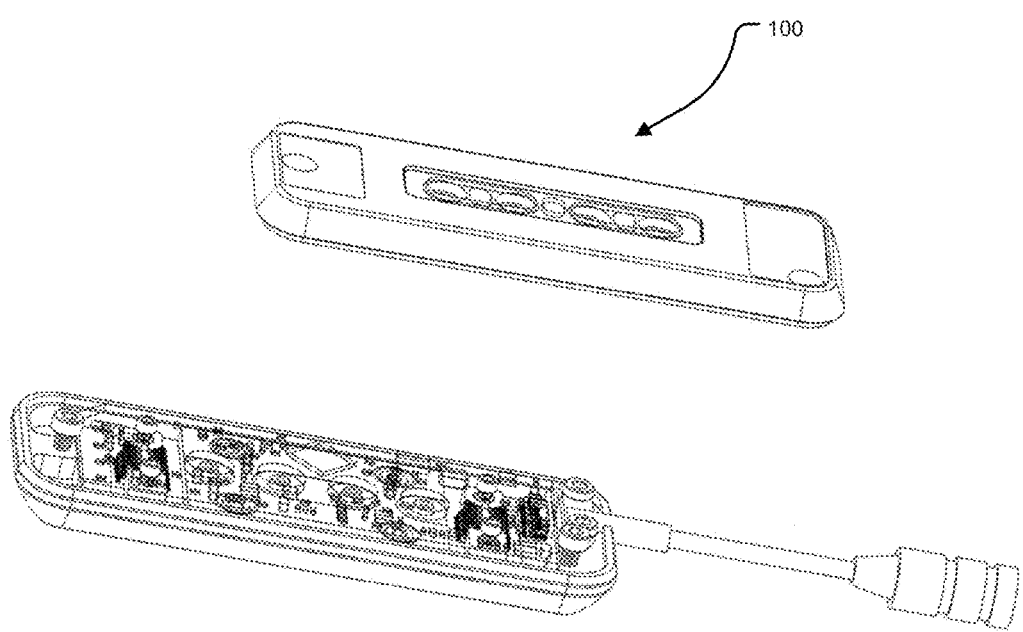
FIG. 9 is a partially exploded perspective view of the FIG. 7 light applicator.
Figure 10:
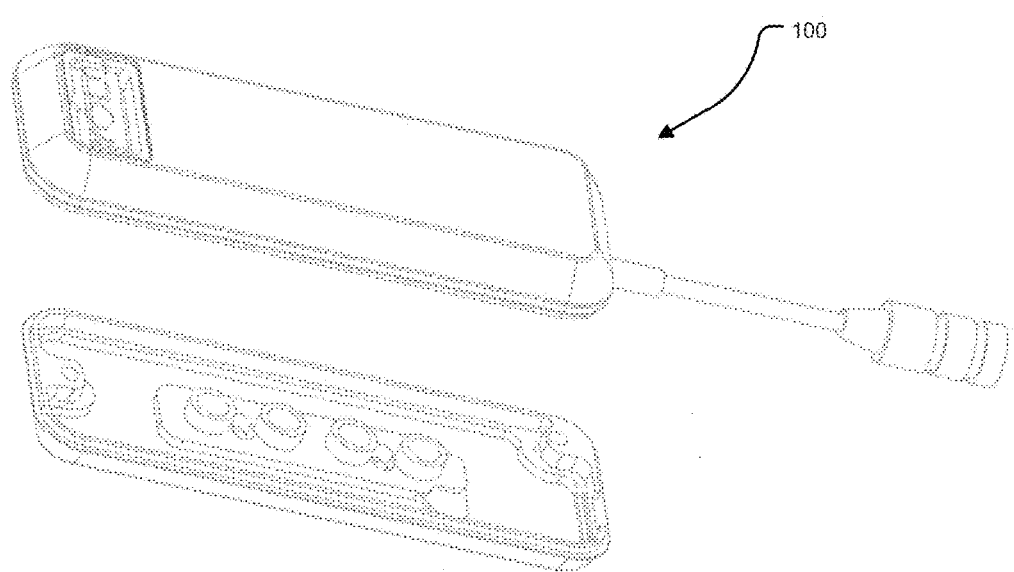
FIG. 10 is a partially exploded perspective view of the FIG. 7 light applicator.

As best seen in FIGS. 5 and 6, treatment plate 22 comprises one or more bosses 34 disposed on an inner side thereof. Bosses 34 may be in the shape of hollow cylinders. The outer diameter of bosses 34 may be small enough to allow bosses 34 to pass through the corresponding apertures in control PCB 16. The inner diameter of bosses 34 may be big enough to accommodate the corresponding laser diode 28 which may extend into boss 34. Bosses 34 extend through the apertures in control PCB 16 to be in physical contact with heat spreader plate 30. Heat spreader plate 30 is held in positive contact with bezel portions 36 of laser diodes 28 to ensure good thermal contact and heat dissipation between heat spreader plate 30 and laser diodes 28. The contact paths from laser diodes 28 (via bezels 36) to heat spreader plate 30 and to treatment plate 22 (via bosses 34) create heat conduction paths to enable heat generated by laser diodes 28 to be effectively transferred to treatment plate 22. When light applicator 10 is held in positive contact with a subject's body surface during treatment, heat is transferred from treatment plate 22 to the subject's body. Heat spreader plate 30 and/or treatment plate 22 are made of a thermally conductive material or thermally conductive materials, e.g., aluminum, copper, or the like.

The interlocking arrangement of diode PCB 12, heat spreader plate 30, control PCB 16 and bosses 34 of treatment plate 22 can provide a low-profile form factor. In the illustrated embodiment, control PCB 16 comprises a plurality of apertures which receive the corresponding plurality of bosses 34 extending from treatment plate 22. Also heat spreader plate 30 comprises a plurality of apertures which receive the corresponding plurality of laser diodes 28 extending from diode PCB 12. Therefore, the presence of control PCB 16 and heat spreader plate 30 do not necessarily increase the thickness of light applicator 10. Also, control PCB 16 is located in a space between treatment plate 22 and heat spreader plate 30, and is protected by being sandwiched between treatment plate 22 and heat spreader plate 30.

The dual board (PCB) architecture (i.e., having a control PCB and a diode PCB separate from one another) is advantageous. It allows a control PCB to potentially work with different diode PCBs having various numbers of laser diodes or other solid-state light emitters. For example, a control PCB does not have to change if the design of the diode PCB changes from an 8-laser to 12-laser configuration. The dual board (PCB) structure also significantly improves ease of serviceability. For example, in the case that a laser diode fails, a service technician to swap out the diode PCB. This could also reduce costs as the diode PCB which is swapped out does not carry control components. In some embodiment, it is also possible to have two or more diode PCB's, and each one of the two or more diode PCB's may carry one or more laser diodes.

One aspect of the invention relates to a light applicator which incorporates a closed-loop feedback system. For example, the closed-loop feedback system may comprise one or more sensors to monitor outputs or some other performance parameters of the light emitters. The closed-loop feedback system may also comprise a control unit. The sensors may be integrated with the light emitters. Such sensors may be light sensors, optical sensors or some other suitable sensors. The sensors transmit information relating to the outputs or some other performance parameters of the light emitters to the control unit in the light applicator. The control unit uses the information to control and/or modulate the light emitters.

Individual light emitters may be calibrated at the point of manufacture. For example, a measurement device may be used to individually measure the light output of the light emitters for one or more sets of driving conditions. The light output may vary because of light emitter manufacturing tolerances. During this process, parameters of the driving signal applied to the light emitter may be varied until the measurement device reads the required output value. Once this is reached, a "set-point" corresponding to the amount of power to achieve the required output value is saved, e.g., in a non-volatile memory in the light applicator. In operation, the sensors continuously monitor the light output of the light emitters and the control unit uses the information from the sensors to make dynamic changes where required to ensure that a desired light output is maintained for the light emitters, e.g., over the life of the light emitters. The sensors may be used to continuously monitor each one of the light emitters individually. If the output of a light emitter weakens, the control unit will dynamically increase the amount of power to the light emitter in order to normalize light output to the "set-point".

In some embodiments, the light applicator may be calibrated using a 2-setpoint calibration protocol. In such a protocol, light output of a light emitter is measured at a first current, and also measured at a second current which is different from the first current. Based on these two measurements, a function (e.g., a linear function) may be generated to determine what light output is expected for some different current (e.g., a current between the first current and the second current).

With the closed-loop feedback feature, the sensors may sense one or more parameters of the light emitters and send signals to the control unit in the light applicator, which enables the performance of each individual light emitter to be monitored continuously or periodically or intermittently. Each light emitter's current is dynamically adjusted by the control unit such that the light output of the light emitter is adjusted to a desired value or within a desired range. The closed-loop feedback feature provides a number of advantages. For example, it mitigates any variable performance characteristics of the light emitters; it mitigates the effect of declining light output over the lifetime of each light emitter; and it mitigates the effect of declining light output caused by heating of the light emitter over the treatment time.

The control unit may also process the information from the sensors and cause the information to be recorded in a non-volatile memory in the light applicator. For example, the control unit may cause information relating to light outputs in one or more treatment sessions to be recorded in the non-volatile memory.

One aspect of the invention relates to a light applicator which incorporates anti-loss-of-control features. For example, the output of each light emitter is monitored (e.g., using the closed-loop feedback feature as described above). If a light emitter's output changes suddenly and the change is not expected then the control unit may detect the change and automatically operate a control switch to shut down the light emitter. The closed-loop feedback system may poll the output performance of individual light emitters at frequent intervals. If a large difference ($\Delta$) of light output is detected between one time interval and another, a lock-down function may be initiated by the control unit, turning off all the light emitters immediately. The applicator will go into a "malfunction mode".

One aspect of the invention relates to a light applicator which incorporates diagnostic capabilities and light emitter degradation metrics to ensure consistent treatment and to identify when the light applicator or one or more light emitters need to be replaced due to aging. This may be achieved using the closed-loop feedback system as discussed above. As those skilled in the art would understand, due to the brightness of the light, and/or due to the infrared nature of the light, it is typically not possible to tell by visual examination whether a light emitter has diminished light output—a measuring device needs to be used. Such a measuring device may be incorporated into the light applicator. For example, each of the light emitters may incorporate an integrated optical feedback sensor. Additionally or alternatively, sensors which are external to the light emitters could be used. For example, the photo sensors could be positioned lateral to the light emitter windows in line of sight of the treatment surface. If the sensors detect that the light output at some current is less than a threshold output value, the control unit may automatically shut down the light emitters.

The light applicator according to the present invention may comprise other safety sensor features. For example, the light applicator may comprise one or more thermal sensors. For example, the thermal sensors may be mounted on a printed circuit board, although this is not mandatory. Alternatively, the thermal sensors may be located on the inner side of the treatment plate. The thermal sensors are used to continuously monitor the temperature of the light emitters. The thermal sensors send temperature information to a control unit. The control unit compares the measured temperature with a reference value corresponding to a safety level. If the temperature exceeds the predetermined safety level, the light emitters will be automatically shut down by the control unit. In some embodiments, a thermal pad may be positioned in contact with a part of a housing of the applicator (e.g., the treatment plate). The thermal pad is a hard wired sensor on the power circuit which immediately cuts the power when a predetermined temperature is exceeded.

The light applicator according to the present invention may comprise one or more proximity sensors (e.g., capacitive touch sensors). The proximity sensors may be located on the treatment plate or on a printed circuit board. An example proximity sensor 38 is shown in FIG. 6. In the FIG. 6 embodiment, proximity sensors 38 extend from control PCB 16 and toward treatment plate 22. The proximity sensors are used to ensure that the treatment plate of the light applicator is correctly apposed against a subject's body surface before the light emitter will be turned on. When the treatment plate of the light applicator is properly apposed against the subject's body surface, the proximity sensors will send signals to the control unit to allow the light emitters to be turned on. The control unit will prevent the light emitters from being turned on if the light applicator is not properly placed against the subject's body surface. This provides supplementary eye-protection to the operator and/or the subject.

When the light applicator is not in use, the light applicator may be stowed in a storage unit (e.g., a paddle dock). The paddle dock may be a feature of the light control device. The paddle dock may incorporate a sensor (e.g., a Hall sensor/magnetic field sensor or the like) which detects when the light applicators are (or are not) correctly stowed in the paddle dock. In the event that the light applicator is not detected to be in the paddle dock (and it is not detected to be in contact with the subject's body surface) then the light emitters will not be turned on. Alternatively or additionally, the light applicator may comprise a sensor, such as a magnetic field sensor. One example of a suitable magnetic field sensor is a Hall sensor. Other types of sensors, such as RFID sensor or mechanical switches, could also be suitable. The magnetic field sensor may detect whether the light applicator is stowed in the paddle dock or outside the paddle dock. If the magnetic field sensor detects that the light applicator is in the paddle dock, the magnetic field sensor will send a signal to the control unit in the light applicator (or a processor in the light control device) which in turn will prevent the light emitters from being turned on. Additionally, if the sensor detects that the light applicator is stowed in the paddle dock, the sensor sends signals to the control unit which inhibits the light emitters from being turned on even when the proximity sensors have detected that the light applicator is placed against a nearby surface. This feature addresses the potential issue that the proximity sensors could inadvertently allow the light emitters to be turned on when the light applicator is placed against a surface in the paddle dock.

The light applicator according to the present invention may comprise a communication monitoring sensor. If the communication monitoring sensor detects a loss of communication between the light applicator and the light control device, the sensor sends a signal to the control unit in the light applicator, and the control unit turns off the light emitters.

The light applicator may use lower-power circuit design to minimize heat generated by control components. Much of the heat generated in electronic circuits is produced during conversions between voltage levels. By performing most of the required voltage conversion in the light control device and passing a voltage close to the required operating level to the light applicator, unwanted heat production is reduced significantly in the light applicator. Voltage regulation can be performed in the light control device, thereby limiting the number of components and the amount of heat generated in the light applicator. The voltage applied to the light emitter circuit may be kept as low as possible, consistent with proper operation, to limit heating of the associated components (e.g., control transistors and current sense resistors). The transistor and current sense resistor components form part of the control loop determining the current in the light emitters. The transistor acts as a valve that regulates the amount of current flowing, while the current sense resistor measures the amount of current. Both these components generate heat in proportion to the voltage across them. By limiting the voltage to a low level consistent with proper operation, undesired heat production is reduced. The transistor and current sense resistor components may be mounted on a printed circuit board. In some embodiments, the transistor and current sense resistor components are thermally coupled to the treatment plate. In some other embodiments, the transistor and current sense resistor components are not thermally coupled to the treatment plate.

In some embodiments the light control device is configured to output a variable voltage to the light applicator for driving the light emitters. In some embodiments, the one or more light applicators all receive the same voltage from the external light control device. This voltage level may be set to as low a value as practical, consistent with correct device operation, in order to limit the heat generation in the light applicator. The power supply may be interrupted for all the light applicators at once, using an emergency shutoff switch located on the external light control device.

The light applicator according to the present invention may utilize a fast multi-drop communication protocol to ensure robust and intelligent operation. For example, RS485 may be used. RS485 is relatively immune to data corruption from electrical noise. Additionally or alternatively, other wired or non-wired communications modalities such as ethernet, wi-fi, bluetooth, or the like, may be used to provide communication between the light applicator and the light control device. A well-defined data communication protocol with robust error checking is desirable to ensure that instructions from the control device are correctly received (and interpreted) by the light applicator and vice versa (e.g. "turn on", "turn off", "run at XX mW power level" etc.). Similarly, it is desirable that the light control device receives accurate messages from individual light applicators. A reliable communication protocol is desirable when some or all of the control circuitry resides in the light applicators themselves, rather than in the light control device.

The light applicator may utilize a communication protocol that can auto-detect connection between the light applicator and the light control device very quickly, e.g., within one or two seconds for all light applicators, or 0.2 seconds for one light applicator (e.g., a new communication data packet is sent every 0.2 seconds). This means that the control device is able to remain in "real-time" control and communication with each of the individual light applicators. The protocol may auto-detect disconnection between the light applicator and the light control device in 1 second or less.

In addition to normal treatment operation, the communication protocol may support: factory calibration of individual light emitters on each light applicator and/or factory-uploading of treatment log-files stored within each light applicator. The communication protocol may command certain modes of operation that are useful for calibration but may not be needed during regular operation. For example, individual light emitters may be turned on or off such that their performance can be measured separately from the other emitters in the light applicator. The communication protocol data packet has an extensible format which allows it to be used to communicate and transfer any data that is logged and stored on the light applicator.

In some embodiments, the light applicator incorporates a control unit and a non-volatile memory. The control unit may cause a full history of the use of the light applicator from the first time it is used to be recorded and stored in the non-volatile memory. For example, each light applicator is able to maintain a full history of the performances of the light emitters, the light output of each individual light emitters, and any light emitter failures or malfunctions. This feature is advantageous as it allows a manufacturer or service provider to track how the light applicators are used in the field. When a customer sends a light applicator to the manufacturer or service provider for repair or troubleshooting, the manufacturer or service provider will be able to determine how the light applicator was used and a full history of the performances of the light emitters. The manufacturer or service provider may generate a database based on such information. As this database of knowledge grows, the manufacturer or service provider may be able to provide better services and/or products to customers. In addition, the data in the database may help verify when any failures occurred and/or verify proper operation in case the light applicator did not fail.

Figure 12:
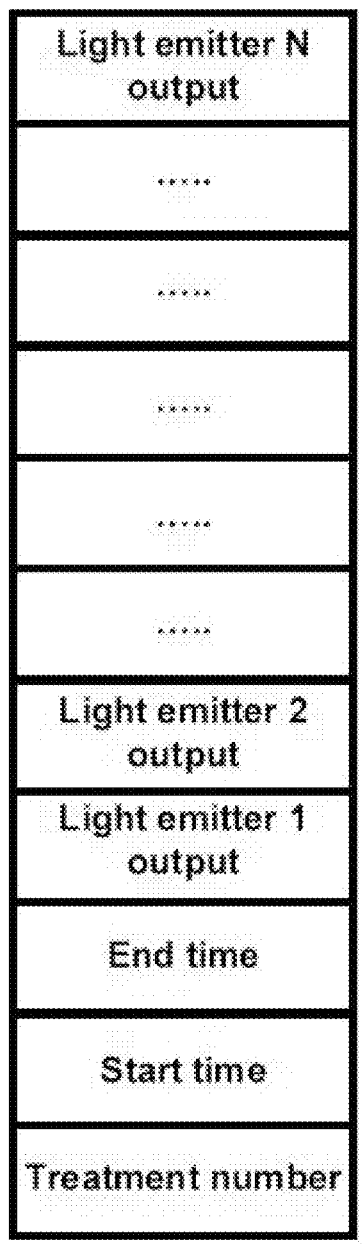
FIG. 12 is a diagram showing an example data structure for recording data in a memory of an example light applicator.
Figure 13:
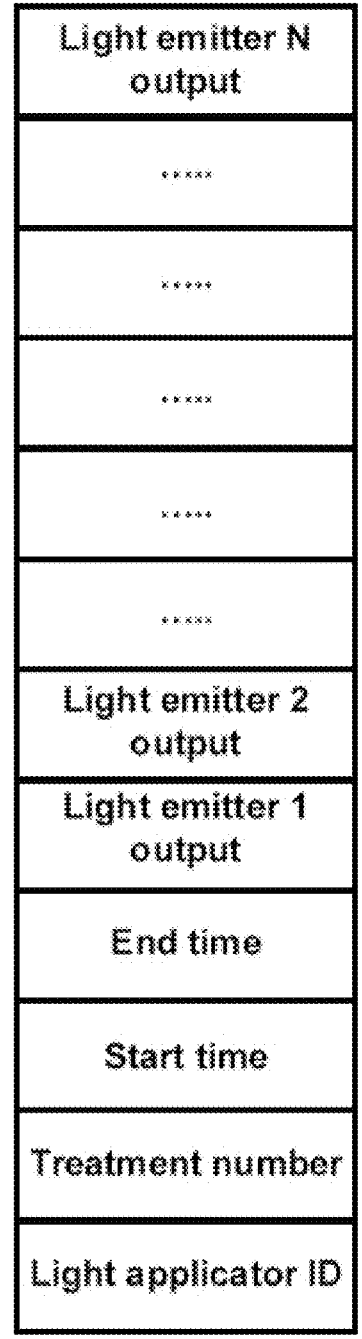
FIG. 13 is a diagram showing an example data structure for recording data in a memory of an example light control device in an example lipolysis system.

The light applicator according to the present invention may also comprise a data-logging feature. The non-volatile memory of the light applicator may be used to maintain a non-volatile log file of all performed treatments. Treatment start and stop times as well as performance parameters of the light emitters may be recorded in the memory in the light applicator. For example, the light applicator memory may record data in a data structure that comprises one or more of the following items: treatment number, start time, end time, light emitter 1 output, light emitter 2 output, . . . , and light emitter N output. An example data structure 300 is schematically shown in FIG. 12. Additionally or alternatively, the light control device may also comprise a non-volatile memory which is used to maintain a non-volatile log file of all performed treatments of all associated light applicators. Treatment start and stop times as well as performance parameters of the light emitters of each associated light applicator may be recorded in the memory of the light control device. The memory of the light control device may record data from a plurality of light applicators. For example, the light control device memory may record data in a data structure that comprises one or more of the following items: light applicator ID, treatment number, start time, end time, light emitter 1 output, light emitter 2 output, . . . , and light emitter N output. An example data structure 400 is schematically shown in FIG. 13. Such a data structure may include additional information such as one or more measured temperatures, an ambient temperature reading, electrical parameters such as voltage and/or current supplied to one or more of the light emitters, times at which an output of a proximity sensor changes, a count of state changes of the proximity sensor during a treatment or the like.

FIGS. 7-10 illustrate a light applicator 100 according to another embodiment of the present invention. Light applicator 100 is similar to light applicator 10 except that light applicator 100 contains 4 laser diodes.

Although some of the embodiments described herein utilize laser diodes as the light emitters, this is not mandatory. Other solid-state light emitters, such as LEDs or some other solid-state light emitters may be used.

Figure 11:
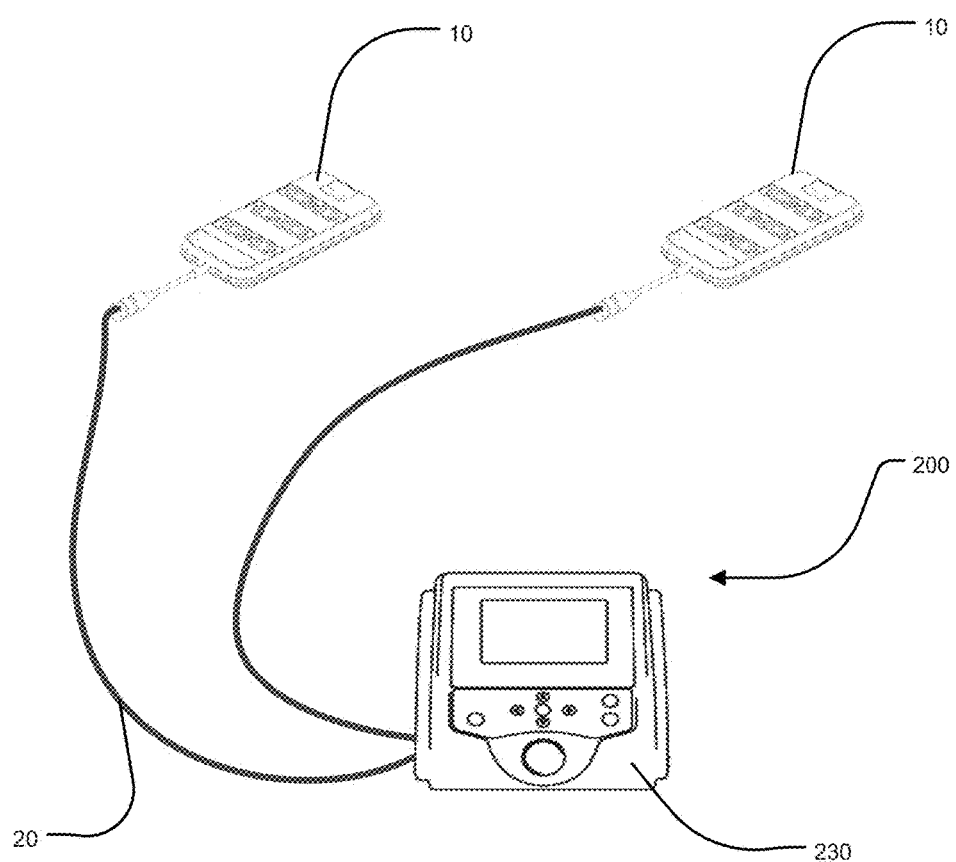
FIG. 11 is a diagram showing a lipolysis system according to an example embodiment of the invention.

An exemplary lipolysis system 200 according to an example embodiment of the present invention is schematically illustrated in FIG. 11. System 200 may comprise one or more light applicators (e.g., light applicator 10) and a light control device 230 configured for communicating and cooperating with the one or more light applicators. Light control device 230 may comprise a power supply, a processor, a memory, circuitry, one or more input units (e.g., buttons, dials, keypad, keyboard, or touchscreen, etc.), and one or more output units (e.g., a display screen). The light control device supplies power to the light emitters of the light applicators. The light control device may also be configured for at least one of generating, transmitting, recording, processing, storing and reporting electronic signals and/or other information useful for modulation of the light emitters.

According to one aspect of the invention, there are provided methods for the use of the lipolysis systems and/or the light applicators of the present invention. In some embodiments, the method comprises contacting the treatment plate of the light applicator with a target portion of a subject's body surface, turning on the light emitters of the light applicator, and providing light irradiation of the target portion of the subject's body portion for a period of time. The method may comprise conducting heat generated from the light emitters via heat conducting members to the treatment plate and further to the subject's body surface. The method may also comprise manipulating a light control device to communicate with the light applicator to regulate the light emitters of the light applicator. The method may comprise manually or automatically modulating the light emitters of the light applicator. Modulating the light emitters of the light applicator may comprise modulating the current and/or voltage and/or some other parameter of the electric power supplied to the light emitters of the light applicator. The method may also comprise monitoring one or more parameters of the light emitter (e.g., light output of the light emitter), sending information to a control unit, and modulating one or more parameters of the light emitters based on the information. The method may comprise modulating the current and/or voltage and/or some other parameter of the electric power supplied to the light emitters to maintain the light output of the light emitters to be at a predetermined value or within a predetermined range. The method may comprise modulating one or more parameters of the light emitters to maintain the light emitters at a predetermined temperature or within a predetermined temperature range. In some embodiments, the method comprises contacting a plurality of light applicators with a plurality of target portions of a subject's body surface for application of light irradiation thereto.

The light applicators, light control devices, and lipolysis systems described herein may optionally be used in accordance with the methods described and illustrated in the commonly-assigned U.S. Pat. No. 7,959,656 and U.S. patent application Ser. No. 11/860,457, which are hereby incorporated by reference herein in their entirety.

This application is intended to cover any variations, uses, or adaptations of the invention using its general principles. Further, this application is intended to cover such departures from the present disclosure as come within known or customary practice in the art to which this invention pertains and which fall within the limits of the appended claims. Accordingly, the scope of the claims should not be limited by the preferred embodiments set forth in the description, but should be given the broadest interpretation consistent with the description as a whole.

What is claimed is:

1. A light applicator configured for contacting a portion of a subject's body surface and applying light irradiation thereto, the light applicator comprising:
   a first printed circuit board;
   one or more light emitters mounted on the first printed circuit board;
   a heat spreader plate adjacent to the first printed circuit board and being in physical contact with the one or more light emitters;
   a thermally conductive treatment plate having an interior surface and an exterior surface, the exterior surface for contacting the portion of the subject's body surface, the treatment plate having one or more windows;
   one or more hollow cylindrical heat conducting members, the one or more heat conducting members between and in contact with the interior surface of the treatment plate and the heat spreader plate, and thermally connecting the treatment plate with the heat spreader plate; and
   a second printed circuit board disposed in a space between the treatment plate and the heat spreader plate, the second printed circuit board having apertures through which the one or more hollow cylindrical heat conducting members extend;

wherein:
the one or more light emitters extend from the first printed circuit board through corresponding one or more apertures on the heat spreader plate and one or more apertures on the second printed circuit board;
the one or more light emitters are configured to project light through the corresponding one or more windows of the treatment plate;
the one or more light emitters are in thermal contact with the treatment plate such that when the light applicator is in use heat generated by the light emitters is conducted to the treatment plate and further to the subject;
the heat spreader plate is configured to provide a heat conduction path from the one or more light emitters to the heat spreader plate, and further to the treatment plate via the one or more heat conducting members; and
the heat spreader plate and the heat conducting members are thermally conductive.

2. The light applicator according to claim 1 wherein the one or more light emitters emit light in the visible spectrum.

3. The light applicator according to claim 1 wherein the one or more light emitters emit light in the infrared spectrum.

4. The light applicator according to claim 1 wherein the one or more light emitters comprise one or more light emitters having a power output in the range of 10 mW to 160 mW.

5. The light applicator according to claim 4 wherein the one or more light emitters comprise one or more light emitters having a power output in the range of 30 mW to 40 mW.

6. The light applicator according to claim 1 wherein each of the light emitters is in physical contact with a wall of a corresponding opening in the heat spreader plate.

7. The light applicator according to claim 1 comprising a closed-loop feedback system, the system comprising a control unit and one or more sensors mounted on the second printed circuit board which are configured to monitor one or more performance parameters of the light emitters.

8. The light applicator according to claim 7 wherein when the sensors detect a light output of a light emitter to be different from a predetermined value or outside a predetermined range, the sensors will transmit signals to the control unit, and the control unit will adjust the amount of power to the light emitter to normalize the light output of the light emitter to the predetermined value or within the predetermined range.

9. The light applicator according to claim 8 wherein each one of the light emitters is monitored individually.

10. The light applicator according to claim 8 wherein the closed-loop feedback system maintains each one of the light emitters to a predetermined value or within a predetermined range.

11. The light applicator according to claim 10 wherein when the sensors detect the light output of a light emitter to be below a threshold value, the control unit automatically shuts down the light emitter.

12. The light applicator according to claim 10 wherein when the sensors detect a change ($\Delta$) of a light output of a light emitter at two different time points to be above a pre-determined value, the control unit automatically shuts down the light emitter.

13. The light applicator according to claim 10 wherein the sensors comprise thermal sensors.

14. The light applicator according to claim 13 wherein when the thermal sensors detect the temperature of a light emitter to be above a pre-determined value, the control unit automatically shuts down the light emitter.

15. The light applicator according to claim 10 wherein the sensors comprise proximity sensors.

16. The light applicator according to claim 15 wherein the proximity sensors permit the light emitters to be turned on only when the treatment plate of the light applicator is placed against a surface.

17. The light applicator according claim 10 wherein the sensors comprise magnetic field sensors.

18. The light applicator according to claim 17 wherein the magnetic field sensors prevent the light emitters from being turned on when the light applicator is stowed in a light applicator storage unit.

19. The light applicator according to claim 1 wherein the light applicator comprises a non-volatile memory and a processor configured to process and write information to the non-volatile memory, wherein the non-volatile memory is configured to store a history of the performances of the light emitters.

20. The light applicator according to claim 1 wherein the windows comprise cutouts in the treatment plate, wherein the windows comprise a material transparent to a light emitted by the light emitter.

21. A system comprising one or more light applicators and a light control device, the light control device comprising hardware and circuitry for controlling the one or more light applicators and for providing power to the one or more light applicators, the one or more light applicators configured for contacting a portion of a subject's body surface and applying light irradiation thereto, the one or more light applicators each comprising:
a first printed circuit board;
one or more light emitters mounted on the first printed circuit board;
a heat spreader plate adjacent to the first printed circuit board and being in physical contact with the one or more light emitters;
a thermally conductive treatment plate having an interior surface and an exterior surface, the exterior surface for contacting the portion of the subject's body surface, the treatment plate having one or more windows;
one or more hollow cylindrical heat conducting members, the one or more heat conducting members between and in contact with the interior surface of the treatment plate and the heat spreader plate, and thermally connecting the treatment plate with the heat spreader plate; and
a second printed circuit board disposed in a space between the treatment plate and the heat spreader plate, the second printed circuit board having apertures through which the one or more hollow cylindrical heat conducting members extend;

wherein:
the one or more light emitters extend from the first printed circuit board through corresponding one or more apertures on the heat spreader plate and one or more apertures on the second printed circuit board;
the one or more light emitters are configured to project light through the corresponding one or more windows of the treatment plate;
the one or more light emitters are in thermal contact with the treatment plate such that when the light applicator is in use heat generated by the light emitters is conducted to the treatment plate and further to the subject;

the heat spreader plate is configured to provide a heat conduction path from the one or more light emitters to the heat spreader plate, and further to the treatment plate via the one or more heat conducting members; and the heat spreader plate and the heat conducting members are thermally conductive.

22. The system according to claim 21 wherein electronic components for voltage conversion are placed in the light control device.

23. The system according to claim 21 wherein the light control device comprises one or more light applicator storage units for stowing the light applicators when the light applicators are not in use, and one or more sensors for keeping the light applicators off when the light applicators are stowed in the light applicator storage units.

24. The system according to claim 21 wherein the light applicators communicate with the light control device using a communication protocol, wherein data packet is sent between the light applicator and the light control device every 0.2 seconds or less.

* * * * *